(12) United States Patent  
Choi et al.

(10) Patent No.: US 9,192,447 B2  
(45) Date of Patent: Nov. 24, 2015

(54) SURGICAL ROBOT SYSTEM AND METHOD OF CONTROLLING THE SAME

(71) Applicant: SAMSUNG ELECTRONICS CO., LTD., Suwon-si, Gyeonggi-do (KR)

(72) Inventors: Byung Kwon Choi, Suwon-si (KR); Kyung Shik Roh, Seongnam-si (KR); Tae Sin Ha, Seongnam-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 120 days.

(21) Appl. No.: 14/050,874

(22) Filed: Oct. 10, 2013

(65) Prior Publication Data

US 2014/0257330 A1    Sep. 11, 2014

(30) Foreign Application Priority Data

Mar. 6, 2013   (KR) .................. 10-2013-0023931

(51) Int. Cl.
*A61B 19/00*   (2006.01)
*B25J 9/16*   (2006.01)

(52) U.S. Cl.
CPC ........... *A61B 19/2203* (2013.01); *B25J 9/1689* (2013.01); *A61B 19/5212* (2013.01); *A61B 2019/2223* (2013.01)

(58) Field of Classification Search
CPC ...... B25J 3/00; B25J 9/1689; A61B 19/2203; A61B 19/5212; A61B 2019/2223; A61B 19/5225

USPC .............. 606/1, 130, 407, 417; 600/424, 427, 600/300; 700/259; 370/464; 382/153

See application file for complete search history.

(56) References Cited

U.S. PATENT DOCUMENTS

| 6,728,599 | B2 * | 4/2004 | Wright et al. ................. 700/258 |
| 8,374,723 | B2 * | 2/2013 | Zhao et al. .................... 700/259 |
| 2012/0053597 | A1 * | 3/2012 | Anvari et al. ................. 606/130 |
| 2012/0071752 | A1 * | 3/2012 | Sewell et al. ................. 600/424 |

FOREIGN PATENT DOCUMENTS

| JP | 2001-346768 | 12/2001 |
| JP | 2002-272758 | 9/2002 |
| KR | 10-2011-0059828 | 6/2011 |

* cited by examiner

*Primary Examiner* — Jonathan W Miles
*Assistant Examiner* — George J Ulsh
(74) *Attorney, Agent, or Firm* — Harness, Dickey & Pierce, P.L.C.

(57) ABSTRACT

A surgical robot system capable of storing all data transmitted and received in the surgical robot system and a method of controlling the same includes a slave device performing surgery on a patient, a master device controlling a surgical operation of the slave device, an imaging device transmitting a medical image regarding the patient to the slave device and the master device, and a monitoring device comprising a storage module receiving all data transmitted and received among the slave device, the master device, and the imaging device, serializing the received data on a per transmission-time-information basis to generate serial packets, and storing the generated serial packets, and a reproduction module dividing the stored serial packets into a plurality of unit packets and transmitting the unit packets to a device for display.

15 Claims, 11 Drawing Sheets

SURGICAL ROBOT SYSTEM AND METHOD OF CONTROLLING THE SAME

CROSS-REFERENCE TO RELATED APPLICATIONS

This application claims the benefit of Korean Patent Application No. 10-2013-0023931, filed on Mar. 6, 2013 in the Korean Intellectual Property Office, the disclosure of which is incorporated herein by reference.

BACKGROUND

1. Field

One or more embodiments relate to a surgical robot system capable of storing all data transmitted and received in the surgical robot system, and a method of controlling the same.

2. Description of the Related Art

Minimally invasive surgery generally refers to surgery capable of minimizing incision size and recovery time. Differently from laparotomy using relatively large surgical incisions through a part of a human body (e.g., the abdomen), in minimally invasive surgery, after forming at least one small incision (or invasive hole) of 0.5 cm to 1.5 cm through the abdominal wall, an operator inserts an endoscope and surgical tools through the incision, to perform surgery while viewing images provided by the endoscope.

Upon comparison with laparotomy, such minimally invasive surgery causes less post-operative pain, faster recovery of bowel movement, earlier restoration of ability to eat, shorter hospitalization, faster return to daily life, and better cosmetic effects owing to small incision size. Due to these properties, minimally invasive surgery is used for cholecystectomy, prostatic carcinoma surgery, hernia repair, and the like, and applications thereof continue to grow.

In general, a surgical robot system used in minimally invasive surgery includes a master device, a slave device, and an imaging device. The master device generates a control signal in accordance with manipulation of a doctor and transmits the control signal to the slave device. The slave device receives the control signal from the master device and performs manipulation required for surgery upon a patient. The master device and the slave device may be integrated or may be separately arranged in an operating room.

The slave device includes at least one robot arm. A surgical instrument is mounted on an end of each robot arm, and in turn a surgical tool is mounted on an end of the surgical instrument.

In minimally invasive surgery using the aforementioned surgical robot, the surgical tool of the slave device and the surgical instrument provided with the surgical tool are introduced into the body of a patient to perform required procedures. In this case, after the surgical tool and the surgical instrument enter the human body, an internal status is visible from images acquired using an endoscope that is an imaging device. In this regard, the master device, the slave device, and the imaging device of the surgical robot system may transmit and receive data such as an image, a sound, a control signal, and status information therebetween through a wired or wireless network, thereby operating.

SUMMARY

Therefore, one or more embodiments relate to a surgical robot system that may improve abilities of performing surgery and system performance through verification of the status of surgery during or after surgery and a method of controlling the same.

Additional aspects and/or advantages of one or more embodiments will be set forth in part in the description which follows and, in part, will be apparent from the description, or may be learned by practice of one or more embodiments of disclosure. One or more embodiments are inclusive of such additional aspects.

In accordance with one or more embodiments, a surgical robot system may include a slave device that may perform surgery on a patient, a master device that may control a surgical operation of the slave device, an imaging device that may transmit a medical image regarding the patient to the slave device and the master device, and a monitoring device that may include a storage module that may receive all data transmitted and received among the slave device, the master device, and the imaging device, may serialize the received data on a per transmission-time-information basis to generate serial packets, and may store the generated serial packets, and a reproduction module that may divide the stored serial packets into a plurality of unit packets and may transmit the unit packets to a device for display.

In accordance with one or more embodiments, a method of controlling a surgical robot system may include receiving data transmitted and received among a master device, a slave device, and an imaging device, generating serial packets by serializing the received data on a per transmission-time-information basis, storing the generated serial packets, and dividing the stored serial packets into a plurality of unit packets and respectively transmitting the divided unit packets to each corresponding device for reproduction.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Figure 1:
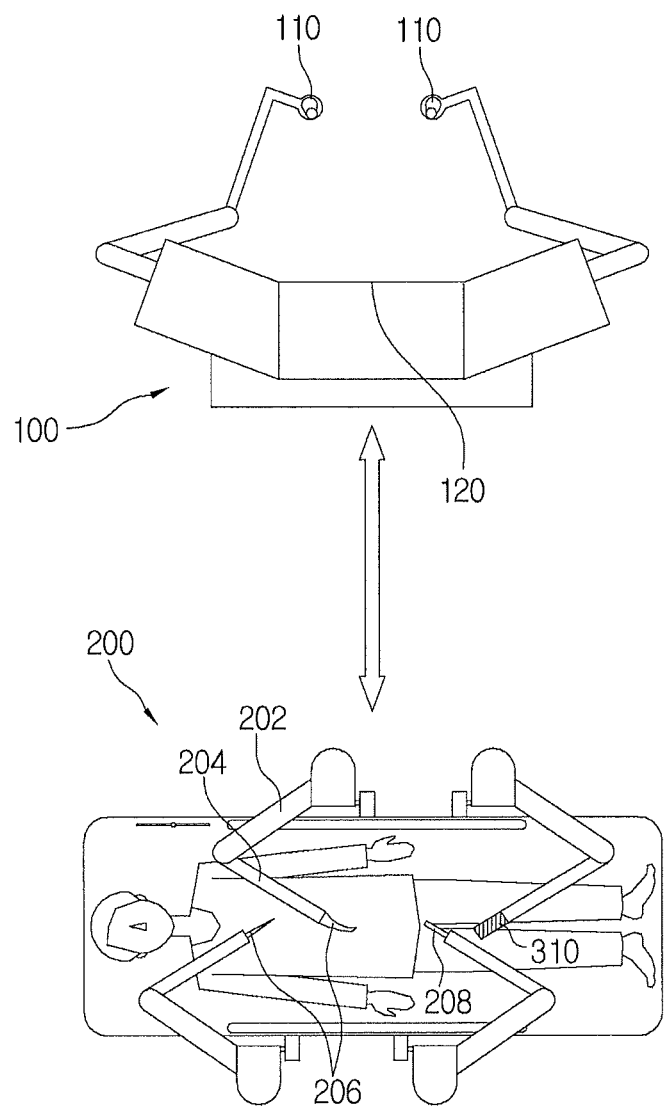
FIG. 1 is a plan view illustrating an outer appearance of a surgical robot according to one or more embodiments.

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention.

Figure 2:
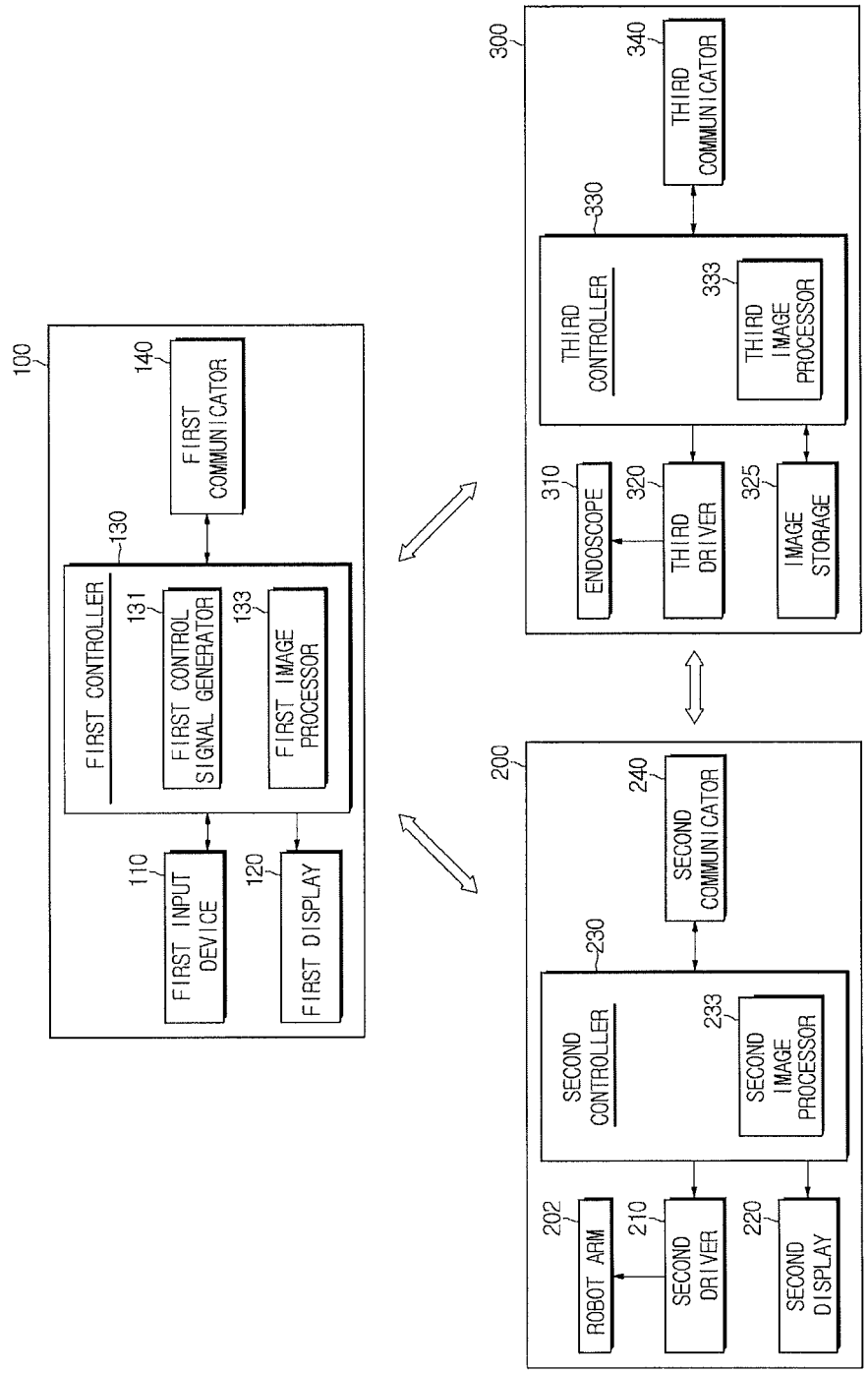
FIG. 2 is a block diagram schematically illustrating constituent elements of a surgical robot system according to one or more embodiments.

FIG. 1 is a plan view illustrating an outer appearance of a surgical robot according to one or more embodiments. FIG. 2 is a block diagram schematically illustrating constituent elements of a surgical robot system according to one or more embodiments.

Referring to FIG. 1, a surgical robot system may include a slave device 200 performing surgery on a patient who lies on an operating table and a master device 100 remotely controlling the slave device 200 in accordance with manipulation of an operator (e.g., a doctor).

According one or more embodiments, the master device 100 and the slave device 200 may be separately arranged as physically independent devices, without being limited thereto. For example, the master device 100 and the slave device 200 may also be integrated with each other as a single device. In addition, FIG. 1 illustrates that the slave device 200 and an imaging device 300 (FIG. 2) including an endoscope 310 may be physically integrated with each other, without being limited thereto. The slave device 200 and the imaging device 300 may be separated from each other as physically independent devices.

Hereinafter, for descriptive convenience, elements constituting the master device 100 are referred to as "first" elements, elements constituting the slave device 200 are referred to as "second" elements, and elements constituting the imaging device 300 are referred to as "third" elements. Thus, the elements of each of the master device 100, the slave device 200, and the imaging device 300 may be distinguished from each other.

As illustrated in FIG. 1, the master device 100 may include a first input device 110 and a first display 120.

The first input device 110 refers to an element that receives an instruction for selection of an operation mode of the surgical robot or an instruction for remote control of operations of the slave device 200, and the like which are input by the operator. In the present embodiment, the first input device 110 may include a haptic device, a clutch pedal, a switch, and a button, but is not limited thereto. For example, a voice recognition device may also be used. Hereinafter, a haptic device will be exemplarily described as an example of the first input device 110.

FIG. 1 exemplarily illustrates that the first input device 110 may include two handles, but the present embodiment is not limited thereto. For example, the first input device 110 may include one handle or three or more handles as well.

The operator may respectively manipulate two of the handles using both hands to control operation of the robot arm 202 of the slave device 200. Although not shown herein, each handle may include an end effector, a plurality of links, and a plurality of joints.

In this regard, the end effector may have a pencil or stick shape with which a hand of the operator may be in direct contact, without being limited thereto.

In addition, a joint refers to a connection between two links and may have 1 degree of freedom (DOF), or greater. Here, "degree of freedom (DOF)" refers to a DOF with regard to kinematics or inverse kinematics. A DOF of a mechanism indicates to the number of independent motions of a mechanism or the number of variables that determine independent motions at relative positions between links. For example, an object in a 3D space defined by X-, Y-, and Z-axes has at least one DOF selected from the group consisting of 3 DOFs to determine a spatial position of the object (a position on each axis), 3 DOFs to determine a spatial orientation of the object (a position on each axis), and 3 DOFs to determine a spatial orientation of the object (a rotation angle relative to each axis). More specifically, when an object is movable along each of X-, Y-, and Z-axes and is rotatable about each of X-, Y-, and Z-axes, it will be appreciated that the object has 6 DOFs.

In addition, a detector (not shown) may be mounted on the joint. The detector may detect information indicating the state of the joint, such as force/torque information applied to the joint, position information of the joint, and speed information while moving. Accordingly, in accordance with manipulation of the first input device 110 by the operator, the detector may detect information regarding the status of the manipulated first input device 110 and transmit the detected information regarding the status of the first input device 110 to a first controller 130 illustrated in FIG. 2. In addition, a first control signal generator 131 of the first controller 130 may generate a control signal corresponding to the status information of the first input device 110 received from the detector, and the generated control signal may be transmitted to the slave device 200 through a first communicator 140.

That is, the first controller 130 of the master device 100 may generate the control signal corresponding to the detected status information of the first input device 110 according to manipulation by the operator using the first control signal generator 131 and transmit the generated control signal to the slave device 200 using the first communicator 140.

The first display 120 of the master system 100 may display a real image acquired by the endoscope 310 of the imaging device 300, a 3D image generated using a medical image of a patient before surgery, or a virtual image generated by projecting the 3D image onto the real image acquired by the endoscope 310, and the like. To this end, the first controller 130 of the master device 100 may include a first image processor 133 that receives image data from the imaging device 300 and outputs the image data to the first display 120. In this regard, "image data" may be a real image acquired by the endoscope 310 of the imaging device 300, a 3D image generated using a medical image of a patient before surgery, or a virtual image generated by projecting the 3D image onto the real image acquired by the endoscope 310 as described above, but is not limited thereto.

The first display 120 may include at least one monitor, and each monitor may be implemented to individually display information required for surgery. For example, when the first display 120 includes three monitors, one of the monitors may display image data received from the imaging device 300, i.e., a real image acquired by the endoscope 310, a 3D image generated using a medical image of a patient before surgery, or a virtual image generated by projecting the 3D image onto the real image acquired by the endoscope 310, and the other two monitors may respectively display information regarding the status of motion of the slave system 200 and information regarding the patient. In this regard, the number of monitors may vary according to the type and kind of information to be displayed.

Here, "information regarding the patient" may refer to information indicating vital signs of the patient, for example, bio-information such as body temperature, pulse, respiration, and blood pressure. In order to provide such bio-information to the master system 100, the slave system 200, which will be described later, may further include a bio-information measurement device that may include, for example, a body temperature-measuring module, a pulse-measuring module, a respiration-measuring module, a blood pressure-measuring module, and the like. To this end, the first controller 130 of the master system 100 may further include a signal processor (not shown) to receive bio-information from the slave system 200, process the bio-information, and output the processed information to the first display 120.

The slave device 200 may include a plurality of robot arms 202, a surgical instrument 204 mounted on one end of each robot arm 202, and a surgical tool 206 or 208 mounted on one end of the surgical instrument 204. In this regard, although not illustrated in FIG. 1, the slave device 200 may further include a body (not shown) to which the plurality of robot arms 202 is coupled. The body (not shown) may fix and support the robot arms 202.

In addition, although not illustrated in FIG. 1, the plurality of robot arms 202 may include a plurality of links and a plurality of joints. Each of the joints may connect links and may have 1 DOF or greater. Here, since the DOF has been described above in detail with reference to the first input device 110 of the master system 100, a detailed description thereof will not be given.

In addition, a second driver 210 operating according to a control signal received from the master system 100 may be mounted on each of the joints of the robot arm 202. For example, when the operator manipulates the first input device 110 of the master system 100, the master system 100 may generate a control signal corresponding to the status information of the manipulated first input device 110 and may transmit the control signal to the slave system 200, and a second controller 230 of the slave system 200 may drive the second driver 210 in accordance with the control signal received from the master system 100, so as to control motion of each joint of the robot arm 202. Here, a substantial control process such as rotation and movement in a direction corresponding to the robot arm 202 in accordance with manipulation of the first input device 110 by the operator does not fall within the scope of the present invention, and thus a detailed description thereof will not be given.

Meanwhile, each joint of the robot arm 202 of the slave system 200 may move according to the control signal received from the master system 100 as described above. However, the joint may also move by external force. That is, an assistant positioned near the operating table may manually move each of the joints of the robot arm 202 to control the location of the robot arm 202, or the like.

Although not illustrated in FIG. 1, the surgical instrument 204 may include a housing mounted on an end of the robot arm 202 and a shaft extending from the housing by a predetermined length.

A drive wheel (not shown) may be coupled to the housing. The drive wheel may be connected to the surgical tools 206 and 208 via a wire, or the like, and the surgical tools 206 and 208 may be driven via rotation of the drive wheel. To this end, an actuator may be mounted on one end of the robot arm 202 for rotation of the drive wheel. However, the operating mechanism of the surgical tools 206 and 208 is not necessarily constructed as described above, and various other electrical/mechanical mechanisms to realize required motions for the surgical tools 206 and 208 may also be applied thereto.

Examples of the surgical tools 206 and 208 may include, for example, a skin holder, a suction line, a scalpel, scissors, a grasper, a needle holder, a stapler, a cutting blade, and the like, without being limited thereto. However, any known instruments required for surgery may also be used.

In general, the surgical tools 206 and 208 may be classified into main surgical tools and auxiliary surgical tools. Here, "main surgical tools" may refer, for example, to surgical tools performing direct surgical motion, such as cutting, suturing, cauterizing, and rinsing of the surgical region and may include a scalpel or surgical needle. "Auxiliary surgical tools" may refer, for example, to surgical tools that do not perform direct surgical operations on the surgical region and assist motion of the main surgical tools and may include a skin holder.

As illustrated in FIG. 2, the slave device 200 may further include a second display 220 to display a virtual image acquired by projecting a 3D image generated using image data transmitted from the imaging device 300, i.e., a medical image acquired before surgery, onto a real image captured by the endoscope 310. To this end, the second controller 230 of the slave device 200 may include a second image processor 233 to receive image data received from the imaging device 300 and output the image data to the second display 220.

As illustrated in FIG. 2, the imaging device 300 may include an endoscope 310 to acquire a real image of a surgical region of a human body and a third driver 320 to drive the endoscope 310. The imaging device 300 may further include an image storage 325 in which 3D images of medical images captured before surgery may be stored. In this regard, "medical image" may be, for example, a computed tomography (CT) image, a magnetic resonance imaging (MRI) image, a positron emission tomography (PET) image, a single photon emission computed tomography (SPECT) image, an ultrasonography (US) image, or the like, without being limited thereto. To this end, the imaging device 300 may further include a 3D image converter (not shown) to convert the medical image before surgery into a 3D image.

A third controller 330 of the imaging device 300 may receive the control signal from the master device 100, thereby controlling operation of the endoscope 310, such as position, moving direction, speed, and the like by the third driver 320. In addition, the third controller 330 of the imaging device 300 may include a third image processor 333 to generate a virtual image by projecting a 3D image stored in the image storage unit 325 onto a real image acquired by the endoscope 310.

The imaging device 300 may be integrated with the slave device 200 as illustrated in FIG. 1. However, the present embodiment is not limited thereto, and the imaging device 300 and the slave device 200 may be separately arranged as independent separate devices. In this regard, the endoscope 310 may include various surgical endoscopes, such as, for example, a laparoscope, a thoracoscope, an arthroscope, a rhinoscope, a cysotoscope, a rectoscope, a duodenoscope, a cardioscope, and the like. In addition, the endoscope 310 may be a complementary metal-oxide semiconductor (CMOS) camera or a charge coupled device (CCD), but is not limited thereto. Furthermore, the imaging device 300 may further include a lighting device (not shown).

The master device 100, the slave device 200, and the imaging device 300 may construct a network. In this case, the network may be implemented, for example, as a wired network, a wireless network, or any combination thereof. According to such networks, data may be transmitted and received among the master device 100, the slave device 200, and the imaging device 300.

For example, the master device 100 may transmit a control signal to the slave device 200 and the imaging device 300 via the network. In this regard, the "control signal" may be generated by the first control signal generator 131 of the first controller 130 in accordance with the status information of the first input device 110 manipulated by the operator as described above. For example, the "control signal" may include a control signal for adjustment of position and operation of the surgical tools 206 and 208 coupled to the surgical instrument 204 of the slave device 200 and a control signal for adjustment of the position of the endoscope 310 of the imaging device 300, but is not limited thereto. In this regard, when the respective control signals are transmitted simultaneously or at similar times, the control signals may be transmitted independently of each other.

Here, "independent" transmission of the respective control signals may refer to no interference between the control signals, and may also refer to that any one control signal has no effect on the other control signal. To ensure independent transmission of the plurality of control signals, various methods, for example, transmission of additional header data regarding the respective control signals, transmission of the respective control signals based on a generation sequence thereof, or transmission of the control signals based on a preset order of priority, may be used.

The slave device 200 may transmit a signal, which may indicate the status information of operation in accordance with the control signal received from the master device 100, to the master device 100 via the network. The slave device 200 may transmit bio-information such as body temperature, pulse, respiration, and blood pressure to the master device 100 as described above.

In addition, the master device 100 and the slave device 200 may transmit and receive an audio signal therebetween. Here, "audio signal" may include communication between the operator manipulating the master device 100 and the assistant assisting the surgical operation near the slave device 200 or a warning sound to warn about emergencies occurring during the surgical operation, but is not limited thereto. To this end, although not illustrated in FIG. 2, the master device 100 and the slave device 200 may respectively include a sound input device and a sound output device. Here, the sound input device may be a microphone, and the sound output device may be a speaker, without being limited thereto. In addition, the first controller 130 of the master device 100 and the second controller 230 of the slave device 200 may further include a sound processor to process the sound input by the sound input device and transmit the processed sound to the corresponding device, respectively.

The imaging device 300 may transmit an image signal to the master device 100 and the slave device 200 via the network. Here, the image signal may include a 3D image generated using a medical image of the patient before surgery, such as a CT image or an MRI image, a real image of the surgical region of the patient acquired by the endoscope 310, and a virtual image generated by projecting the 3D image onto the real image acquired by the endoscope 310 as described above, but is not limited thereto. In addition, the imaging device 300 may transmit information regarding the operation status of the endoscope 310 in accordance with the control signal of the master device 100 to the master device 100.

As described above, a large amount of data including an image, a sound, a control signal, and status information may be transmitted and received among the master device 100, the slave device 200, and the imaging device 300. Each of the devices may operate according to the received data and output the received data.

Figure 3:
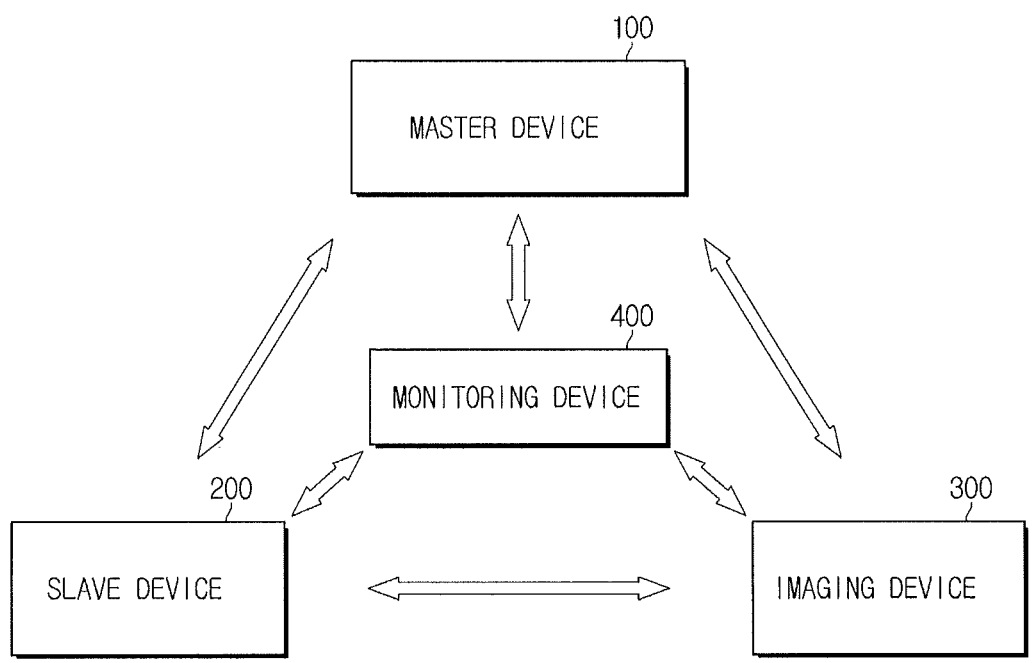
FIG. 3 is a block diagram illustrating an example of a surgical robot system according to one or more embodiments, such as the surgical robot system of FIG. 2, further including a monitoring device.

In one or more embodiments, all data transmitted and received among the master device 100, the slave device 200, and the imaging device 300 may be transmitted to a monitoring device 400 via the network as illustrated in FIG. 3. For example, the master device 100, the slave device 200, and the imaging device 300 may transmit data to the monitoring device 400 while transmitting the data to another device, without being limited thereto. That is, the monitoring device 400 may receive data from each device in real-time, may periodically receive data at predetermined time intervals, or may receive data at once after the surgical operation is completed.

Figure 4:
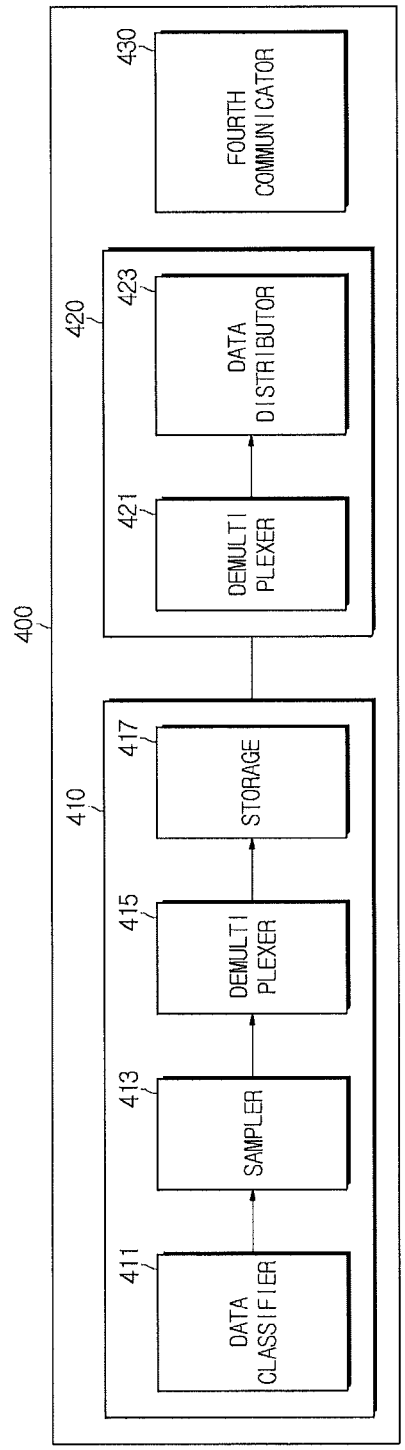
FIG. 4 is a block diagram schematically illustrating constituent elements of a monitoring device according to one or more embodiments.

The monitoring device 400 may receive and store all data transmitted and received among the master device 100, the slave device 200, and the imaging device 300 and may reproduce an image and an operation regarding the status of surgery by transmitting the stored data to each device during or after surgery. As illustrated in FIG. 4, the monitoring device 400 may include a storage module 410, a reproduction module 420, and a fourth communicator 430.

The storage module 410 of the monitoring device 400 may receive all data transmitted and received among the master device 100, the slave device 200, and the imaging device 300 and may classify the data according to type thereof, may sample each of the classified data to generate a plurality of unit packets, may serialize the generated unit packets on a per transmission-time-information basis to generate serial packets, and may store the serial packets.

Figure 5:
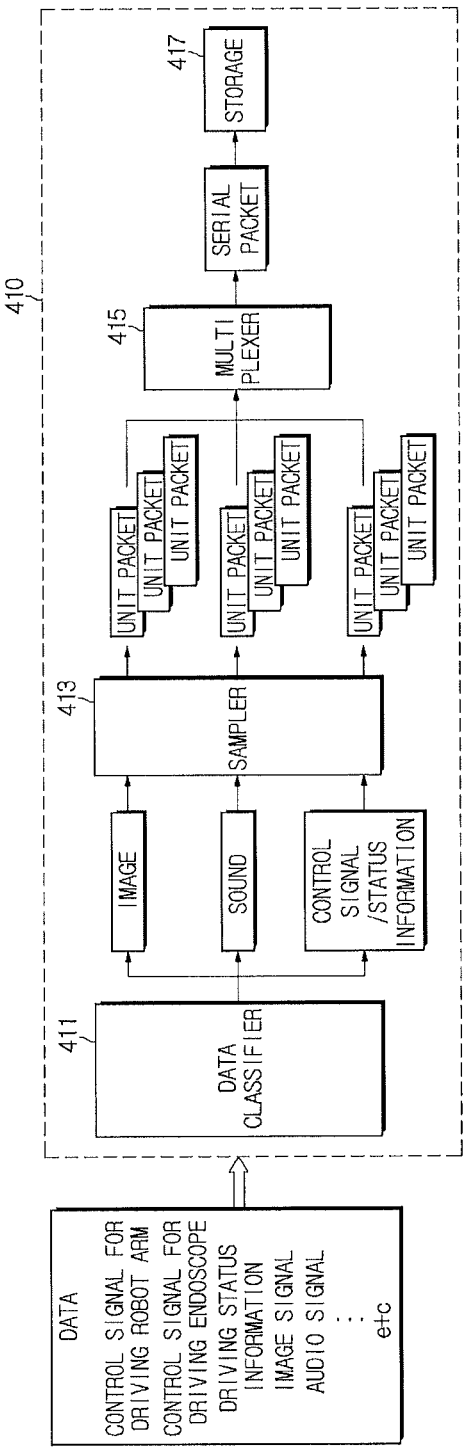
FIG. 5 is a conceptual diagram illustrating operation of a storage module of a monitoring device according to one or more embodiments, such as the monitoring device of FIG. 4.

Particularly, as illustrated in FIGS. 4 and 5, the storage module 410 may classify all data received from the master device 100, the slave device 200, and the imaging device 300 through the fourth communicator 430 using a data classifier 411. In this regard, "all received data" may include a control signal such as a control signal for driving a robot arm and a control signal for driving an endoscope, information regarding driving status according to the control signal, an image signal, an audio signal, and the like, but is not limited thereto. The data classifier 411 may classify the all received data into an image, a sound, a control signal, and status information.

The data, i.e., the image, the sound, the control signal, and status information, classified by the data classifier 411 may be packetized into a plurality of unit packets by a sampler 413. In this regard, the sampler 413 may periodically sample original data at predetermined time intervals into a plurality of unit packets. In this regard, "predetermined time intervals" may refer to a fixed time interval without being limited thereto.

Sampling refers to a process of converting a continuous analog signal such as an image or a sound into a discrete digital signal to obtain required information. That is, when a continuously changing analog signal such as an image and a sound is converted into a digital signal for transmission, there is no need to transmit the entire waveform of the analog signal. Required information is efficiently extracted such that the analog signal does not lose original characteristics thereof and is then transmitted. Sampling is extraction of required information from the original analog signal at predetermined time intervals.

In this regard, the sampling may be performed according to frames per second (FPS), control period, and the like, based on the type of data, without being limited thereto. Here, "FPS" refers to the number of frame per second. In general, when 25 to 30 frames are reproduced per second, the image may be recognized as a natural image by human eyes.

In one or more embodiments, the sampler 413 may perform sampling of image data according to FPS and sampling of audio data through a segment corresponding to FPS, without being limited thereto. In addition, the sampler 413 may perform sampling of the control signal and the status information according to a control period.

The plurality of unit packets generated by the sampler 413 may include a header, in which identification information is recorded, and a payload, in which data is recorded, although not illustrated in FIG. 5 in detail. In this regard, "identification information" may include transmission time information and transmission flow direction of data recorded in the corresponding payload, without being limited thereto. For example, "transmission time information" may refer to transmission time of data from the master device 100, the slave device 200, and the imaging device 300. In addition, "transmission flow direction" may refer to a direction in which data is transmitted, such as a direction from the master device 100 to the slave device 200, a direction from the master device 100 to the imaging device 300, a direction from the slave device 200 to the master device 100, a direction from the slave device 200 to the imaging device 300, a direction from the imaging device 300 to the master device 100, and a direction from the imaging device 300 to the slave device 200, but is not limited thereto. The transmission flow direction may also include a direction from one of the master device 100, the slave device 200, and the imaging device 300 to an external server, for example, a central server of a hospital.

The plurality of unit packets generated by sampler 413 may be input to a multiplexer 415. The multiplexer 415 may serialize the input unit packets on a per transmission-time-information basis stored in each header to generate serial packets.

The multiplexer 415 may be a combination of circuits to select an input corresponding to a predetermined condition among a variety of input lines and output the selected input as a single output line. The multiplexer 415 may be simply referred to as a "MUX". In addition, since the multiplexer 415 may select required data among a plurality of input data and may output a piece of data, it is also be referred to as a data selector. According to one or more embodiments, the multiplexer 415 may select unit packets meeting predetermined conditions, i.e., predetermined transmission time information, among the plurality of input unit packets, serialize the selected unit packets, and may output the serial packets.

Figure 6:
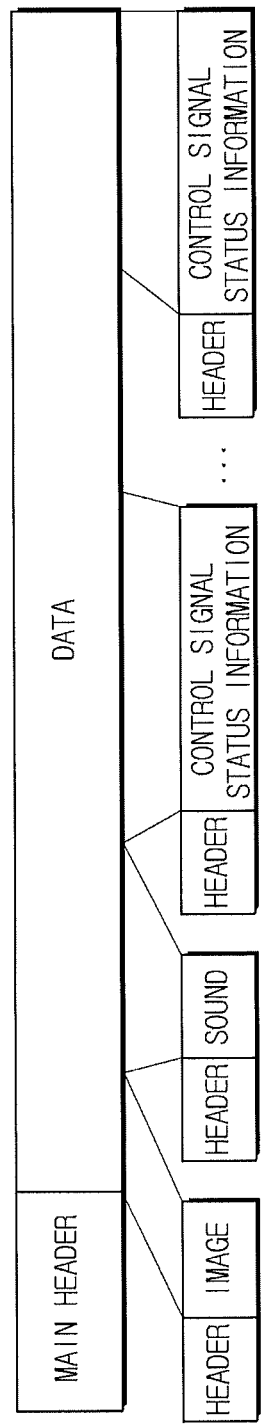
FIG. 6 is a diagram illustrating a serial packet according to one or more embodiments, such as the serial packet of FIG. 5.

As described above, the serial packets generated by the multiplexer 415 may have a structure as illustrated in FIG. 6. Referring to FIG. 6, the serial packet generated according to the present embodiment may include a main header which may include a sequence number, an identifier, and the like and a payload which may include a complex data stream including image-related unit packets, sound-related unit packets, control signals, and status information-related unit packets. In this regard, "sequence number" may include generation time and generation order of the serial packet or storage time and storage order of the serial packet, but is not limited thereto. In addition, "identifier" may indicate that the serial packet is data related to the surgical robot system.

In addition, as illustrated in FIG. 6, "complex data stream" may include a plurality of unit packets. Here, transmission time information of the unit packets may match. In addition, FIG. 6 exemplarily illustrates that the complex data stream may include, for example, one image unit packet, one sound unit packet, and a plurality of unit packets each including one control signal and status information. However, the complex data stream may include a plurality of image unit packets and a plurality of sound unit packets. The serial packets generated as described above may be stored in the storage unit 417.

The storage module 410 of the monitoring device 400 according to one or more embodiments has been described. Although the storage unit 417 may be contained in the storage module 410, the storage unit 417 may be disposed separately from the storage module 410 in the monitoring device 400.

Figure 7:
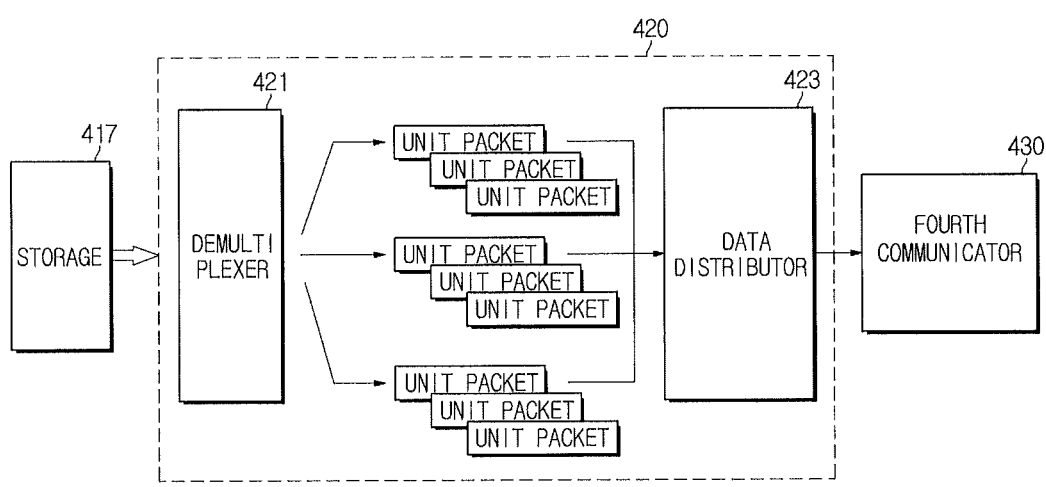
FIG. 7 is a conceptual diagram illustrating operation of a reproduction module of a monitoring device according to one or more embodiments, such as the monitoring device of FIG. 4.

As illustrated in FIGS. 4 and 7, the reproduction module 420 of the monitoring device 400 may include a demultiplexer 421, which may read serial packets from the storage unit 417, divide the serial packets into a plurality of unit packets, and classify the divided unit packets according to type thereof, and a data distributor 423, which may transmit the classified unit packets to a corresponding device selected from the group consisting of the master device 100, the slave device 200, and the imaging device 300 in accordance with the transmission time information and transmission flow direction stored in each header. In this regard, the data distributor 423 may transmit the unit packets to each device through the fourth communicator 430.

That is, the monitoring device 400 of the surgical robot system according to one or more embodiments may receive all of a control signal transmitted from the master device 100 manipulated by an operator during surgery to the slave device 200 and the imaging device 300, e.g., a control signal for driving a surgical tool and a control signal for driving an endoscope, status information according to the control signal transmitted from the slave device 200 and the imaging device 300 to the master device 100, an image signal including an endoscopic image of a surgical region of a patient and a 3D image of the inside of the patient's body transmitted from the imaging device 300 to the master device 100 and the slave device 200, and an audio signal transmitted from the master device 100 to the slave device 200 of from the slave device 200 to the master device 100. Then, the monitoring device 400 may serialize all of the data on a per transmission-time-information basis to generate and store serial packets, divide each of the stored serial packets into a plurality of unit packets during or after surgery, transmit each of the unit packets to the corresponding device according to the transmission time information and transmission flow direction stored in each of the unit packets, so as to possibly reproduce the surgical operation in each device.

For example, the slave device 200 may receive corresponding unit packets from the monitoring device 400 and may reproduce operation of the surgical tool performed during surgery. The master device 100 may receive corresponding unit packets from the monitoring device 400 and may display an image of the surgical operation on the first display 120.

The structure and operation of the surgical robot system including the monitoring device 400 according to one or more embodiments has been described in detail. Meanwhile, although FIG. 4 exemplarily illustrates that the monitoring device 400 may be disposed separately from the master device 100, and the slave device 200, and the imaging device 300, the monitoring device 400 may also be disposed in any one of the master device 100, the slave device 200, and the imaging device 300.

Figure 8:
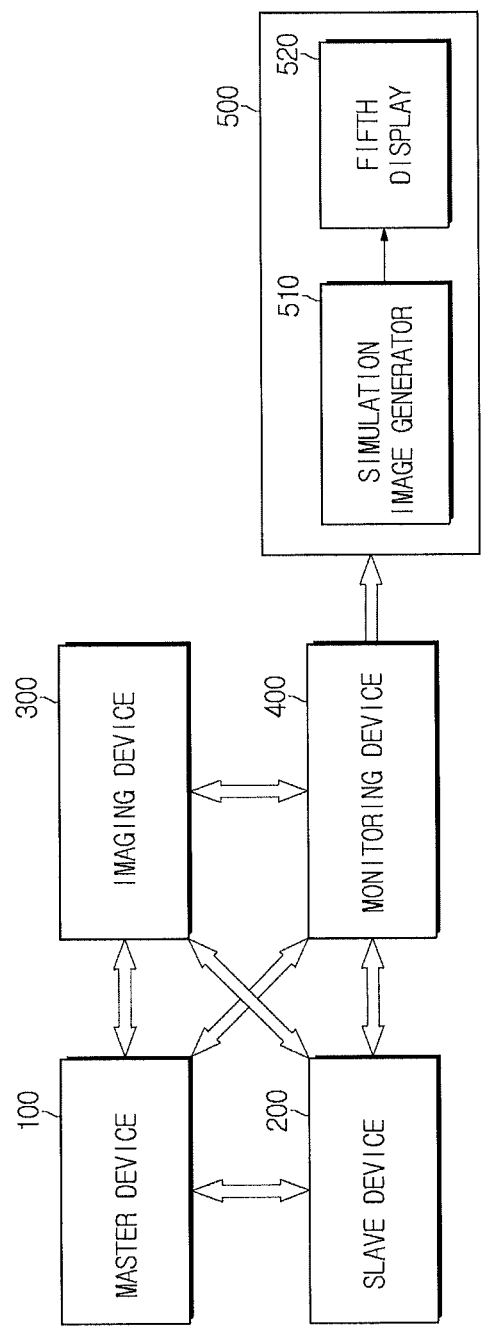
FIG. 8 is a block diagram illustrating a surgical robot system according to one or more embodiments, such as the system of FIG. 3 further including a simulator.

In addition, the surgical robot system according to one or more embodiments may further include a simulator 500 as illustrated in FIG. 8. The simulator 500 may be a device that may receive the plurality of unit packets from the reproduction module 420 of the monitoring device 400, generate a simulation image reproducing the surgical operation, and display the simulation image. The simulator 500 may include a simulation image generator 510 generating the simulation image using the received unit packets and outputting the simulation image and a fifth display 520 receiving the simulation image output from the simulation image generator 510 and displaying the simulation image, but is not limited thereto. For example, the simulator 500 may further include a sound output device (not shown) to output a sound.

In addition, although not shown in FIG. 8, the simulator 500 may further include a manipulator (not shown) manipulated by a trainee. The trainee may practice surgical operation by manipulating the manipulator (not shown).

Meanwhile, FIG. 8 exemplarily illustrates that a simulator according to one or more embodiments may be aligned separately from the master device 100, the slave device 200, the imaging device 300, and the monitoring device 400. However, the imaging device 300 may include a simulation image generator (not shown) and transmit a generated simulation image to the master device 100 to be displayed on the first display 120 of the master device 100, so that a trainee may practice by manipulating the first input device 110 of the master device 100.

As described above, in the surgical robot system according to one or more embodiments, all data transmitted and received among the master device 100, the slave device 200, and the imaging device 300 during surgery may be packetized and stored, and the stored data may be transmitted to each device during or after surgery to reproduce the surgical operation and the status of surgery. As a result, abilities of performing surgery and system performance may be improved through verification of surgery and analysis of the status of surgery.

Figure 9:
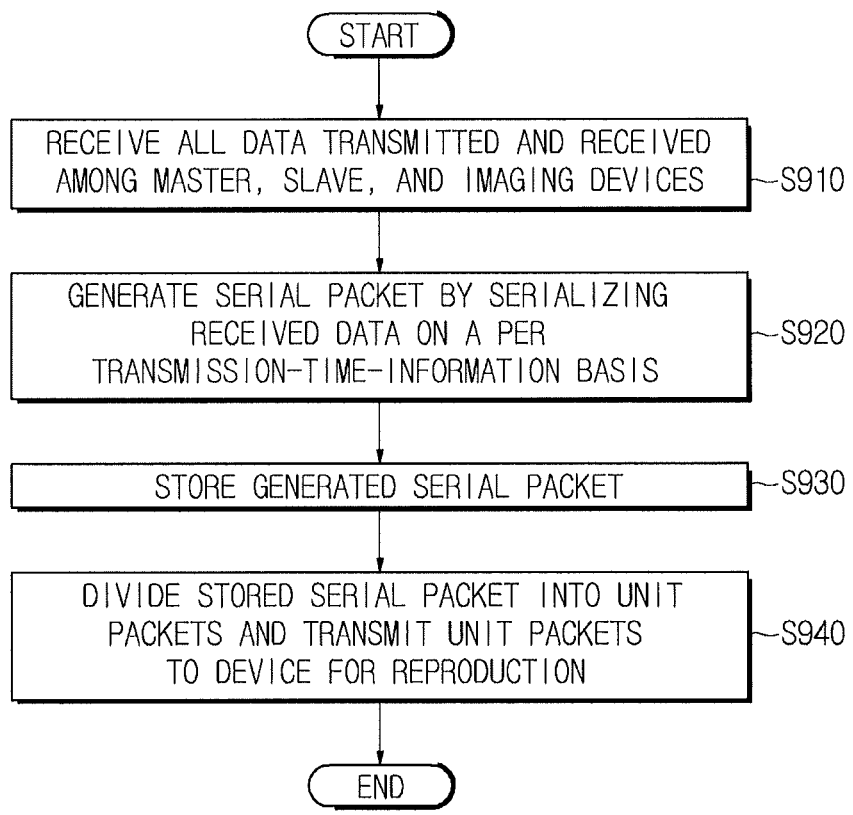
FIG. 9 is a flowchart illustrating a method of controlling a surgical robot system according to one or more embodiments.

FIG. 9 is a flowchart illustrating a method of controlling a surgical robot system according to one or more embodiments. Hereinafter, a method of controlling the surgical robot system will be described in detail with reference to FIGS. 1 to 8.

First, all data transmitted and received among the master device 100, the slave device 200, and the imaging device 300 may be received by a monitoring device 400 (S910). In this regard, a method of transmitting and receiving data among the master device 100, the slave device 200, and the imaging device 300 may include a streaming method by which data is received in real-time and a buffering method by which data is periodically received at predetermined time intervals or received at once after the surgical operation is completed, but is not limited thereto.

In addition, the received data may include an image, a sound, a control signal, and status information, but is not limited thereto. Here, "image" may include a real image acquired by the endoscope 310 of the imaging device 300, a 3D image generated using a medical image of a patient before surgery, or a virtual image generated by projecting the 3D image onto the real image acquired by the endoscope 310, but is not limited thereto. In addition, "sound" may include communication between the operator manipulating the master device 100 and the assistant assisting the surgical operation near the slave device 200 or a warning sound to warn about emergencies occurring during the surgical operation, but is not limited thereto.

In addition, "control signal" may include a control signal for adjustment of position and operation of the surgical tools 206 and 208 coupled to the surgical instrument 204 of the slave device 200 and a control signal for adjustment of the position of the endoscope 310 of the imaging device 300, but is not limited thereto. "Status information" may include information regarding the status of operation in accordance with the control signal (e.g., operation completion, operation error, and the like), and bio-information such as body temperature, pulse, respiration, and blood pressure, but is not limited thereto.

Then, the received data may be serialized to generate serial packets on a per transmission-time-information basis (S920), and the generated serial packets may be stored in the storage unit 417 (FIG. 5) (S930). Here, the received data may include an image, a sound, a control signal, and status information, as described above. Accordingly, the aforementioned process may include the following operations as illustrated in FIG. 10.

Figure 10:
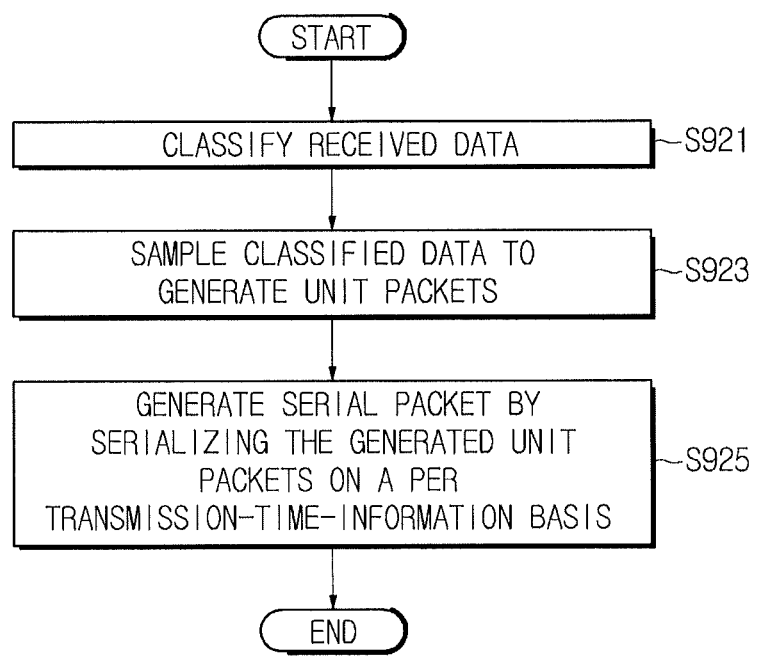
FIG. 10 is a flowchart illustrating generating a serial packet according to one or more embodiments in detail.

Referring to FIG. 10, the received data may be classified according to the type of data (S921). Here, "classifying according to the type of data" may refer to classifying of data in accordance with determination as to whether the received data is an image, a sound, a control signal, or status information.

Then, the classified data may be sampled to generate a plurality of unit packets (S923). In this case, the sampling may be periodically performed at predetermined intervals. Here, "predetermined intervals" may refer to a fixed time interval without being limited thereto.

Sampling refers to a process of converting a continuous analog signal such as an image or a sound into a discrete digital signal to obtain required information. That is, when a continuously changing analog signal such as an image and a sound is converted into a digital signal for transmission, there is no need to transmit the entire waveform of the analog signal. Required information is efficiently extracted such that the analog signal does not lose original characteristics thereof and is then transmitted. Sampling is extraction of required information from the original analog signal at predetermined time intervals.

In this regard, the sampling may be performed according to frames per second (FPS), control period, and the like, based on the type of data, without being limited thereto. For example, when data is an image or a sound, the data may be sampled according to FPS. When, data is a control signal or status information, the data may be sampled according to control period.

The plurality of unit packets generated by sampling may respectively include a header in which identification information is recorded and a payload in which data is recorded. Here, "identification information" may include transmission time information and transmission flow direction of data recorded in the payload, but is not limited thereto.

In this regard, "transmission time information" may refer to transmission time of data from the master device 100, the slave device 200, and the imaging device 300. In addition, "transmission flow direction" refers to a direction in which data is transmitted, such as a direction from the master device 100 to the slave device 200, a direction from the master device 100 to the imaging device 300, a direction from the slave device 200 to the master device 100, a direction from the slave device 200 to the imaging device 300, a direction from the imaging device 300 to the master device 100, and a direction from the imaging device 300 to the slave device 200, but is not limited thereto. The transmission flow direction may also include a direction from one of the master device 100, the slave device 200, and the imaging device 300 to an external server, for example, a central server of a hospital.

Then, the generated unit packets may be serialized on a per transmission-time-information basis to generate serial packets (S925). Here, generation of the serial packets may be performed by the multiplexer 415 illustrated in FIG. 5, without being limited thereto.

The multiplexer 415 may be a combination of circuits to select an input corresponding to a predetermined condition among a variety of input lines and output the selected input as a single output line. The multiplexer 415 may be simply referred to as a "MUX". In addition, since the multiplexer 415 may select required data among a plurality of input data and outputs as a piece of data, it may also be referred to as a data selector. According to one or more embodiments, the multiplexer 415 may select unit packets meeting predetermined conditions, i.e., predetermined transmission time information, among the plurality of input unit packets, serialize the selected unit packets, and output the serial packets.

As described above, the serial packets generated by the multiplexer 415 may have a structure as illustrated in FIG. 6. Referring to FIG. 6, the serial packets generated according to the present embodiment may respectively include a main header including a sequence number, an identifier, and the like and a payload having a complex data stream including image-related unit packets, sound-related unit packets, and unit packets related to control signal and status information. In this regard, "sequence number" may include generation time and generation order of the serial packet or storage time and storage order of the serial packet, but is not limited thereto. Here, "sequence number" may include generation time and generation order of the serial packet or storage time and storage order of the serial packets, but is not limited thereto. In addition, "identifier" may indicate that the serial packet is data related to the surgical robot system.

In addition, as illustrated in FIG. 6, a "complex data stream" may include a plurality of unit packets. Here, transmission time information of the unit packets may match. In addition, FIG. 6 exemplarily illustrates that the complex data stream may include one image unit packet, one sound unit packet, and a plurality of unit packets each including one control signal and status information. However, the complex data stream may also include a plurality of image unit packets and a plurality of sound unit packets.

Figure 11:
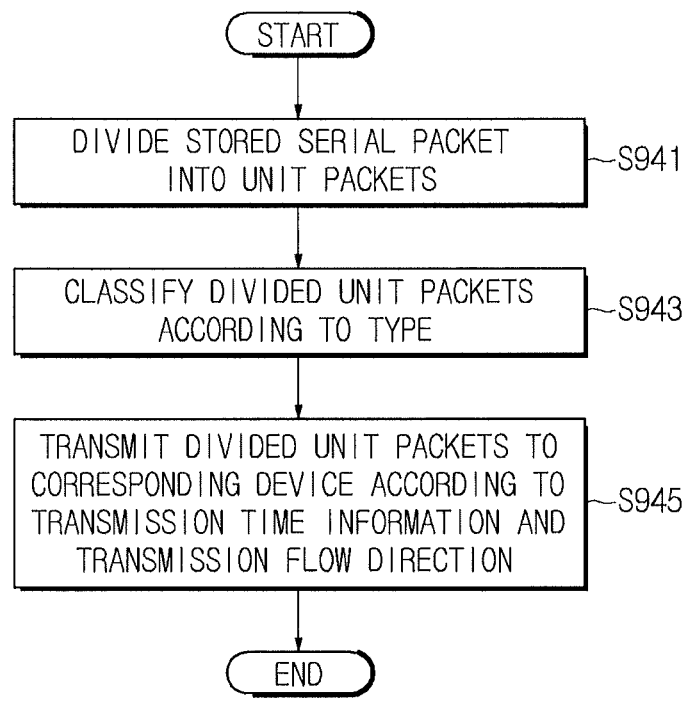
FIG. 11 is a flowchart illustrating dividing a serial packet according to one or more embodiments in detail.

Then, the stored serial packets may be divided into a plurality of unit packets and transmitted to a device for reproduction (S940). The aforementioned process may include the following operations as illustrated in FIG. 11.

First, the stored serial packets may be divided into a plurality of unit packets (S941), and the divided unit packets are classified according to the type thereof (S943). This operation may be performed by the demultiplexer 421 illustrated in FIG. 7, without being limited thereto. Then, the classified unit packets may be transmitted to a corresponding device according to transmission time information and transmission flow direction information recorded in each header, i.e., one device selected from the group consisting of the master device 100, the slave device 200, and the imaging device 300 (S945).

As described above, the method of controlling the surgical robot system according to the one or more embodiments may include receiving all data including a control signal, status information, an image signal, and an audio signal. The control signal may be transmitted from the master device 100 manipulated by the operator to the slave device 200 and the imaging device 300 during surgery and may include a control signal for driving the surgical tools and a control signal for driving the endoscope. The status information may indicate status of operation in accordance with the control signal and may be transmitted from the slave device 200 and the imaging device 300 to the master device 100. The image signal may be transmitted from the imaging device 300 to the master device 100 and the slave device 200 and may include an image of the surgical region of the patient acquired by the endoscope and a 3D image of the patient's body. The audio signal may be transmitted from the master device 100 to the slave device 200 or transmitted from the slave device 200 to the master device 100. According to the method, the received data may be serialized on a per transmission-time-information basis to generate serial packets, and the serial packets may be stored.

Then, the stored serial packets may be divided into a plurality of unit packets during or after surgery. The divided unit packets are transmitted to the corresponding device in accordance with the recorded transmission time information and transmission flow direction. As a result, the surgical operation may be reproduced in each device.

In addition, the unit packets may be transmitted to the simulator 500 (FIG. 8). The simulator 500 may be a device that receives the plurality of unit packets from the reproduction module 420 of the monitoring device 400, generates a simulation image reproducing the surgical operation, and displays the simulation image. The simulator 500 may include a simulation image generator 510 generating the simulation image using the received unit packets and outputting the simulation image and a fifth display 520 receiving the simulation image output from the simulation image generator 510 and displaying the simulation image, but is not limited thereto. For example, the simulator 500 may further include a sound output device (not shown) to output a sound.

In addition, although not illustrated in FIG. 8, the simulator 500 may further include a manipulator (not shown) manipulated by a trainee. The trainee may practice the surgical operation by manipulating the manipulator (not shown).

In one or more embodiments, any apparatus, system, element, or interpretable unit descriptions herein include one or more hardware devices or hardware processing elements. For example, in one or more embodiments, any described apparatus, system, element, retriever, pre or post-processing elements, tracker, detector, encoder, decoder, etc., may further include one or more memories and/or processing elements, and any hardware input/output transmission devices, or represent operating portions/aspects of one or more respective processing elements or devices. Further, the term apparatus should be considered synonymous with elements of a physical system, not limited to a single device or enclosure or all described elements embodied in single respective enclosures in all embodiments, but rather, depending on embodiment, is open to being embodied together or separately in differing enclosures and/or locations through differing hardware elements.

In addition to the above described embodiments, embodiments can also be implemented through computer readable code/instructions in/on a non-transitory medium, e.g., a computer readable medium, to control at least one processing device, such as a processor or computer, to implement any above described embodiment. The medium can correspond to any defined, measurable, and tangible structure permitting the storing and/or transmission of the computer readable code.

The media may also include, e.g., in combination with the computer readable code, data files, data structures, and the like. One or more embodiments of computer-readable media include: magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Computer readable code may include both machine code, such as produced by a compiler, and files containing higher level code that may be executed by the computer using an interpreter, for example. The media may also be any defined, measurable, and tangible distributed network, so that the computer readable code is stored and executed in a distributed fashion. Still further, as only an example, the processing element could include a processor or a computer processor, and processing elements may be distributed and/or included in a single device.

The computer-readable media may also be embodied in at least one application specific integrated circuit (ASIC) or Field Programmable Gate Array (FPGA), as only examples, which execute (e.g., processes like a processor) program instructions.

While aspects of the present invention have been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A surgical robot system comprising: a slave device performing surgery on a patient; a master device controlling a surgical operation of the slave device; an imaging device transmitting a medical image regarding the patient to the slave device and the master device; and a monitoring device comprising: a storage module receiving all data transmitted among the slave device, the master device, and the imaging device, serializing the received data on a per transmission-time-information basis to generate a plurality of serial packets, and storing the generated serial packets; and a reproduction module dividing the stored serial packets into a plurality of unit packets and transmitting the unit packets to a device for reproduction, and wherein the storage module comprises: a data classifier classifying the received data according to the type of data; a sampler generating the plurality of unit packets by respectively sampling the classified data; a multiplexer generating the plurality of serial packets by serializing the generated plurality of unit packets on a per transmission-time information basis; and a storage unit storing the generated serial packets.

2. The surgical robot system according to claim 1, wherein the sampler samples the data according to frames per second (FPS) or a control period according to a data type of the classified data.

3. The surgical robot system according to claim 1, wherein the plurality of unit packets respectively comprises a header in which identification information is recorded and a payload in which data is recorded.

4. The surgical robot system according to claim 3, wherein the identification information comprises transmission time information and transmission flow direction information of the data recorded in the payload.

5. A surgical robot system comprising: a slave device performing surgery on a patient; a master device controlling a surgical operation of the slave device; an imaging device transmitting a medical image regarding the patient to the slave device and the master device; and a monitoring device comprising: a storage module receiving all data transmitted among the slave device, the master device, and the imaging device, serializing the received data on a per transmission-time-information basis to generate a plurality of serial packets, and storing the generated serial packets; and a reproduction module dividing the stored serial packets into a plurality of unit packets and transmitting the unit packets to a device for reproduction, and wherein the reproduction module comprises: a demultiplexer dividing the stored serial packets into the plurality of unit packets and classifying the divided unit packets according to the data type of each unit packet; and a data distributor respectively transmitting the classified unit packets to at least one of the slave device, the master device and the imaging device in accordance with the transmission time information and transmission flow direction information.

6. The surgical robot system according to claim 1, wherein each serial packet among the serial plurality of packets comprises a main header and a plurality of unit packets.

7. The surgical robot system according to claim 6, wherein the main header comprises at least one of identification information, generation time, generation order, storage time, and storage order.

8. The surgical robot system according to claim 6, wherein the plurality of unit packets comprises one image unit packet, one sound unit packet, and a plurality of unit packets each comprising control signal and status information.

9. The surgical robot system according to claim 6, wherein the plurality of unit packets comprises a plurality of image unit packets, a plurality of sound unit packets, and a plurality of unit packets each comprising control signal and status information.

10. The surgical robot system according to claim 1, wherein the monitoring device is contained in one device selected from the group consisting of the slave device, the master device, and the imaging device.

11. The surgical robot system according to claim 1, further comprising a simulator receiving the plurality of unit packets from the reproduction module, generating a simulation image, and displaying the simulation image.

12. The surgical robot system according to claim 1, wherein:
the imaging device comprises a simulation image generator receiving the plurality of unit packets from the reproduction module to generate a simulation image and outputting the generated simulation image; and
the master device comprises a display receiving the simulation image output from the simulation image generator of the imaging device and displaying the simulation image.

13. A monitoring device for a surgical robot system comprising: a storage module receiving all data transmitted among a slave device, a master device, and an imaging device, serializing the received data on a per transmission-time-information basis to generate a plurality of serial packets, and storing the generated serial packets; and a reproduction module dividing the stored serial packets into a plurality of unit packets and transmitting the unit packets to a display device, and wherein the storage module comprises: a data classifier classifying the received data according to the type of data; a sampler generating the plurality of unit packets by respectively sampling the classified data; a multiplexer generating the plurality of serial packets by serializing the generated plurality of unit packets on a per transmission-time information basis; and a storage unit storing the generated serial packets.

14. The monitoring device according to claim 13, further comprising a simulator receiving the plurality of unit packets from the reproduction module, generating a simulation image, and displaying the simulation image.

15. A monitoring device for a surgical robot system comprising: a storage module receiving all data transmitted among a slave device, a master device, and an imaging device, serializing the received data on a per transmission-time-information basis to generate a plurality of serial packets, and storing the generated serial packets; and a reproduction module dividing the stored serial packets into a plurality of unit packets and transmitting the unit packets to a display device, and wherein the reproduction module comprises: a demultiplexer dividing the stored serial packets into the plurality of unit packets and classifying the divided unit packets according to the data type of each unit packet; and a data distributor respectively transmitting the classified unit packets to at least one of the slave device, the master device and the imaging device in accordance with the transmission time information and transmission flow direction information.

* * * * *